(12) United States Patent
Cady

(10) Patent No.: US 8,795,238 B2
(45) Date of Patent: Aug. 5, 2014

(54) ADAPTIVE DEVICES FOR SECURING MEDICAL ARTICLES

(75) Inventor: Timothy B. Cady, Encinitas, CA (US)

(73) Assignee: Ivio Medical, LLC, Solana Beach, CA (US)

( * ) Notice: Subject to any disclaimer, the term of this patent is extended or adjusted under 35 U.S.C. 154(b) by 0 days.

(21) Appl. No.: 13/320,025

(22) PCT Filed: Mar. 11, 2011

(86) PCT No.: PCT/US2011/000461
§ 371 (c)(1),
(2), (4) Date: Nov. 10, 2011

(87) PCT Pub. No.: WO2011/112265
PCT Pub. Date: Sep. 15, 2011

(65) Prior Publication Data
US 2012/0059330 A1 Mar. 8, 2012

Related U.S. Application Data

(60) Provisional application No. 61/313,035, filed on Mar. 11, 2010.

(51) Int. Cl.
*A61M 5/32* (2006.01)
*A61M 25/02* (2006.01)

(52) U.S. Cl.
CPC ....... *A61M 25/02* (2013.01); *A61M 2025/0266* (2013.01); *A61M 2025/0253* (2013.01)
USPC .......................................... 604/179; 604/180

(58) Field of Classification Search
USPC ......... 604/178–180; 128/103.1, 123.1, 124.1; 248/49, 65, 73, 74.1, 74.3
See application file for complete search history.

(56) References Cited

U.S. PATENT DOCUMENTS

| 3,146,778 A | 9/1964 | Krawiec | |
|---|---|---|---|
| 3,203,653 A * | 8/1965 | Hall | 248/62 |

(Continued)

FOREIGN PATENT DOCUMENTS

JP           06026592      *  2/1994  ...................... 248/49

OTHER PUBLICATIONS

JP06026592, Nishioku et al., "Piping and wiring duct" Feb. 1, 1994, (English abstract, 2 pages).*

*Primary Examiner* — Quynh-Nhu H Vu
(74) *Attorney, Agent, or Firm* — Acuity Law Group, P.C.; Daniel M. Chambers

(57) ABSTRACT

Adaptive medical article securement devices are described. These devices retain a medical article, for example, a catheter hub or a connector fitting, in position on a patient's body and reduce or inhibit longitudinal or other movement of the medical article. The securement device includes an adaptive retainer and at least one anchor pad used to attach the securement device to a patient's skin. The adaptive retainer is a flexible element that can adapt and conform to an exterior portion of the medical article to be secured, and in doing so forms a central channel in which at least a portion of the medical article becomes disposed. In some embodiments the retainer includes at least one engaging element that can engage a retention element disposed on the medical article. The engaging element, alone or in conjunction with the retention element and/or the shape (e.g., tapering) of the central channel, reduces or inhibits longitudinal motion of the medical article in the central channel.

15 Claims, 5 Drawing Sheets

(56) References Cited

U.S. PATENT DOCUMENTS

| | | | |
|---|---|---|---|
| 3,368,564 A * | 2/1968 | Selix | 604/180 |
| 3,677,250 A | 7/1972 | Thomas | |
| 3,826,254 A * | 7/1974 | Mellor | 604/180 |
| 4,165,748 A * | 8/1979 | Johnson | 604/180 |
| 4,744,535 A * | 5/1988 | Patenaude | 248/74.1 |
| 4,976,698 A | 12/1990 | Stokley | |
| 5,664,769 A * | 9/1997 | Sadinsky et al. | 256/73 |
| 7,014,627 B2 | 3/2006 | Bierman | |
| 7,799,001 B2 | 9/2010 | Bierman | |
| 2009/0178703 A1* | 7/2009 | Gumm | 136/244 |

\* cited by examiner

ADAPTIVE DEVICES FOR SECURING MEDICAL ARTICLES

RELATED APPLICATION

This application claims the benefit of and priority to U.S. provisional patent application Ser. No. 61/313,035, filed 11 Mar. 2010, which, where allowed, is hereby incorporated by reference in its entirety for any and all purposes.

BACKGROUND OF THE INVENTION

1. Introduction.

The following description includes information that may be useful in understanding the present invention. It is not an admission that any such information is prior art, or relevant, to the presently claimed inventions, or that any publication specifically or implicitly referenced is prior art.

2. Background.

Modern medical practice frequently involves using catheters to introduce fluids and medications directly into a patient's vasculature. Examples include peripheral intravenous catheters (PIVCs) and central venous catheters (CVCs). Often, it is necessary to maintain such catheterization over an extended period during a patient's treatment, particularly when the patient is hospitalized. In order to keep a catheter (or other medical line) properly positioned for as long as needed, the catheter (or other medical line) is typically secured to the patient in a variety of ways. Historically this involved taping the catheter or medical line to the patient.

Securing catheters to patient using tape, however, has several drawbacks. First, the use of tape to secure a catheter can retain dirt or other contaminants at or near the catheter insertion site, potentially leading to infection or other complications. Indeed, numerous clinical studies have implicated improperly secured catheters in a wide range of complications, including catheter-related blood stream infections (CRBSI), of which there are about 80,000 annually in the U.S. alone. Second, tape often fails to limit catheter movement in one or more directions, and thus can contribute to motion-related complications such as bruising, phlebitis, extravasation, infiltration, and catheter migration, which can lead to catheter dislodgement or disconnection. Third, tape removal can itself cause undesired catheter movement. Fourth, tape must periodically be changed, often daily. The frequent removal and reapplication of adhesive tape can irritate a patient's skin, as well as lead to the build up of adhesive residue on the outer surface of the catheter (or other medical line). Such adhesive residue not only makes the catheter (or other medical line) stickier and more difficult for healthcare providers to handle, it can also result in contaminants (including pathogens) adhering to the catheter itself, increasing the likelihood of infection, either at the skin surface or internally. Fifth, tape securement can allow medical lines attached to a catheter to flex or kink, which can lead to clinical complications.

As a result of these drawbacks, other approaches to securing catheters and medical lines have been sought. One such solution is reported in U.S. Pat. Nos. 7,014,627 and 7,799,001. However, such devices themselves have many drawbacks, including high unit cost, the use of hard plastic components (which can lead to patient discomfort), requirements for bulky packaging because of the device's awkward three-dimensional shape, difficulty in using such devices, and the need for hospitals to stock large inventories because individual devices are not adaptable to fit the wide range of different catheters and medical articles routinely in use today.

For these reasons a significant unmet need still exists for inexpensive, low-profile, easy-to-use medical article securement devices.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

The term "adaptive" refers a device's or structure's ability to adapt and substantially conform to the exterior shape and/or contours of another article, including articles having different exterior dimensions and shapes.

A "medical article" refers to catheters, catheter hubs, medical line connector fittings, luer access devices, medical lines (e.g., tubing intended to deliver fluids to a patient), and the like.

A "patentable" composition, process, machine, or article of manufacture according to the invention means that the subject matter at issue satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically excludes the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

A "plurality" means more than one.

SUMMARY OF THE INVENTION

The devices and methods of the present invention have several features, no single one of which is solely responsible for its desirable attributes. Without limiting the scope of this invention as expressed by the appended claims, its more prominent features will now be summarized. After considering this summary, and particularly after reading the section entitled "Detailed Description of the Invention's Preferred Embodiments," one will understand how the features of this invention provide several advantages over conventional catheter securement approaches.

One aspect of the invention relates to adaptive medical article securement devices. Such devices include an adaptive retainer having a first anchor region spaced from a second anchor region by a flexible, preferably segmented, substantially flat substrate configured to deform to form a central channel about a channel axis upon application of a deforming force. To form the central channel, the flexible, preferably segmented, substantially flat substrate of the adaptive retainer includes a flexible channel forming element, which is preferably comprised of "n" (where "n" is an integer not less than 2) spaced channel hinge elements that define n−1 channel forming segments. The channel hinge elements preferably are living hinges. In embodiments that employ channel hinge elements, the segmented, substantially flat substrate also preferably includes first and second channel boundary hinge elements (preferably also living hinges) between which the plurality of spaced channel hinge elements are disposed, which hen combined with the spaced channel hinge elements define n+1 channel forming segments. Preferably, the channel boundary hinge elements and channel hinge elements are principally located on opposite sides of the substrate, usually with the channel hinge elements being located on the substrate's upper surface and the channel boundary hinge elements being located on the opposite, lower surface of the substrate.

As those in the art will appreciate, deforming the adaptive retainer forms the central channel. This can be accomplished by applying a deforming force to the adaptive retainer. Preferably, the medical article one wishes to retain or secure is present, and preferably used in the deforming process, although this is not required, particularly in the context of embodiments where the adaptive retainer is designed to deform to form a central channel of predetermined size and shape. When the medical article is present, the segmented, substantially flat substrate can be associated with a desired portion of the medical article so that upon application of the deforming force the adaptive article's substrate forms a central channel that retainingly engages the medical article.

The central channel, when formed, may be closed (i.e., the central channel has an arc length of 360 degrees) or open (i.e., the central channel has an arc length of less than 360 degrees, and preferably more than 180 degrees). The central channel also has a distal opening and a proximal opening, and is configured to engage at least a portion of a medical article inserted therein in order to retain the medical article. In preferred embodiments, the central channel, once formed, has a tapered shape. Preferably, the tapered shape of the central channel is designed to complement a cooperatively tapered shape of that portion of the medical article to be secured by the device according to the invention.

In some embodiments, the lower (i.e., skin-facing) surface of each of the first and second anchor regions is coated with an adhesive designed to attach to the device an epidermal layer of a patient. In preferred embodiments, the adhesive coatings are covered by a removable layer that can easily be peeled away or otherwise removed just prior to adhering the device to a desired location on a patient's body. In other embodiments, the adaptive retainer is connected to at least one anchor pad having a lower adhesive surface configured to attach to an epidermal layer of a patient and an upper surface at least a portion of which can be adhered to the first and second anchor regions of the adaptive retainer.

In certain preferred embodiments, the adaptive medical article securement devices of the invention also include at least one engaging element configured to engage a retention element disposed on the surface of the medical article to be secured. The combination of such engaging and retention elements serves to reduce or inhibit movement of the medical article once the securement devices is attached or otherwise adhered to the patient. The sorts of movement that can be inhibited or reduced include longitudinal movement of the medical article in relation to central axis of the central channel, as well pitch, roll, and/or yaw of the medical article in relation to the securement device.

A related aspect of the invention concerns medical article securement systems. Such systems include an adaptive medical article securement device according to the invention and a medical article retained in the central channel thereof.

Still other aspects of the invention relate to various methods of using the instant adaptive medical article securement devices. Such methods include uniting medical articles with complementary adaptive medical article securement devices by deforming such a securement device, before or (preferably) after association with a medical article so that the central channel of the securement device can retainingly engage the medical article. Still other methods involve securing a medical article to a patient using an adaptive medical article securement device according to the invention. Typically such methods are accomplished by uniting a medical article with an adaptive medical article securement device and adhering the device's anchor pad(s) to the patient's skin.

Other aspects, embodiments, features, and advantages of the invention will be apparent from the following drawings, detailed description, and appended claims.

DETAILED DESCRIPTION OF THE INVENTION'S PREFERRED EMBODIMENTS

Figure 1A:
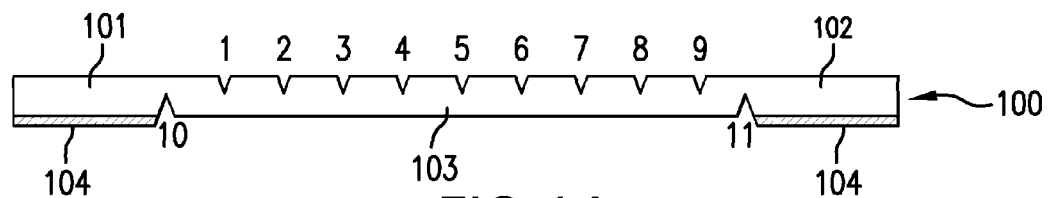
FIG. 1 has three panels, A, B, and C. Panel A is a side view of a representative adaptive medical article securement device according to the invention prior to being adapted to receive a medical article. Panel B is a side view of the securement device shown in Panel A after being adapted to receive a medical article. Panel C is a plan view of the securement device shown in Panel A.

The following description and the accompanying drawings, which describe and show the preferred embodiments, demonstrate several possible representative configurations that an adaptive medical article securement device can take to include various aspects and features the invention. The illustrated embodiments are shown in use with either one or both of an illustrative example of a catheter hub and an illustrative example of a luer access device and extension set connected to the catheter hub. These illustrations are not intended to limit the invention to the specified embodiments or usage. Those skilled in the art will recognize that the described aspects and features of the invention are not limited to any particular embodiment of a securement device, and securement devices according to the invention can readily be designed for use with a variety of medical articles.

To assist in the description of the invention, the following coordinate terms are used. A "longitudinal axis" is generally parallel to a portion of the catheter hub, the connector fitting or other medical article retained by the an adaptive medical article securement device of the invention, as well as parallel to the axis of the central channel of the adaptive retainer, through which the medical article extends. A "lateral axis" is normal or perpendicular to the longitudinal axis. In addition, "longitudinal direction" refers to a direction substantially parallel to the longitudinal axis and "lateral direction" refers to a direction substantially parallel to the lateral axis. The term "axial" refers to the axis of the central channel or connector fitting, and therefore is substantially synonymous with the term "longitudinal" as used herein. Also, the terms "proximal" and "distal", are used consistently, and in context refer to near and far, respectively. The terms "upper," "lower," "top," "bottom," "underside," "upperside" and the like, are used in reference to the orientation of the particular embodiment.

The preferred embodiments of the present invention advantageously provide a adaptive medical article securement device for securing a medical article to a patient. The medical article preferably has an elongated body that cooperates with the adaptive retainer to arrest movement of the medical article in longitudinal, lateral, and other directions when placed within the retainer.

This invention concerns a patentable new generation of patentable adaptive devices for securing medical articles (e.g., medical lines, needles, catheters, etc.) to a patient's skin. Such devices include an adaptive retainer and at least one anchor pad. A medical grade film may also be included. The adaptive securement devices of the invention can be readily adapted to fit a wide range of medical article types, combinations, and dimensions for easy, rapid, and secure attachment to a patient's skin. They are also inexpensive and efficient to manufacture and, because of the adaptive nature of the retainer element, when packaged each device requires minimal storage space and. Finally, the adaptive nature of the retainer element makes them easy to use to secure a medical article.

The flexible, adaptive retainer includes a flexible, optionally segmented, substantially flat substrate disposed between two anchor regions. The substrate incorporates one or more flex elements or hinges (e.g., partial kerfs, grooves, depressions, perforations, and the like) on at least its upper surface (i.e., the surface of the substrate facing away from a patient's skin) and two or more flex elements or hinges on its lower surface (i.e., the substrate's surface facing toward a patient's skin) that allow the initially substantially flat or planar substrate of the adaptive retainer to be bent, molded, folded, or otherwise shaped to conform the external structure(s) of the medical article to be secured when the securement device is brought into contact the medical article(s). The flex elements on the upper surface allow the securement device to be readily adapted to the particular shape and geometry of the external structure of the medical article(s) to be secured. The portion of the adaptive retainer intended for contact or other secure association with a medical article constitutes a medical article contact region, which is disposed in the flexible, optionally segmented, substrate portion of the adaptive retainer. Preferably, the flexible substrate portion contains the at least one flex element on its upper surface. The flexible substrate portion is typically bounded on either end by at least one flex element or hinge located on the lower surface of the adaptive retainer. In many embodiments, the flex elements or hinges on the upper surface are located between the flex element(s) or hinges on the lower surface on either side of the device contact region. In some embodiments, flex elements are found opposite each other on the upper and lower surfaces of at least part of the device. In other embodiments, one or flex elements are not disposed on a surface of the substrate but are disposed within its interior.

In each of the embodiments described below, the adaptive retainer has a flexible, preferably segmented, substantially flat substrate that is deformed to form a central channel. The central channel has a distal opening to allow insertion and withdrawal the medical article to be secured. The medical article is installed or removed from the adaptive retainer via this distal opening. Such an arrangement allows a health care provider to align at least a portion of the medical article with the adaptive retainer before fixing the device to the patient's skin. In this way, the adaptive retainer's central channel retains a portion of the medical article.

The adaptive retainer preferably includes at least one engaging element that cooperates with at least one retention element on the medical article. The one or more engaging elements of the adaptive retainer preferably are disposed normal to the axis of the central channel and can be, for example, a slot, a hole, or like structures. The engaging element cooperates with the one or more retaining elements disposed on the surface of the medical article to inhibit movement of the medical article through or in the channel. For example, the engaging element could be a slot in the substrate disposed to engage at least a portion of a radially extending ridge, post, or other structure protruding from surface of the medical article. In this way, the medical article is limited in longitudinal movement (i.e., movement toward the patient) once the radially extending retaining element engages the slot in the adaptive retainer.

The adaptive retainer of each embodiment described below further includes two anchor regions disposed at opposite ends of the flexible substrate. When adapted to conform to a portion of medical article's exterior surface, the adaptive retainer holds the retained portion of medical article away from the patient's skin, when the retained portion is positioned within the central channel of the adaptive retainer, to avoid chaffing or excoriating the skin. In some preferred embodiments, the articles also include a removal tab disposed at one or both ends of the anchor regions (or anchor pad) to allow for the securement device's easy removal from a patient's skin. Removal tabs typically do not include an adhesive.

The adaptive retainer and anchor regions also can have other constructions to minimize contact between the patient's skin and the adaptive retainer, as well as between the patient and the retained portion of the medical article. For example, the anchor pads can be thicker, in which case the mounting wings can be located higher on the retainer body.

In embodiments have at least two anchor regions, the anchor regions are preferably disposed opposite each other at or near the distal ends of the adaptive retainer and spaced by the flexible, adaptive substrate. The anchor regions also have an adhesive located on the surface intended for skin contact. The adhesive should be suitable for securing the article to a patient and for prolonged skin contact (i.e., for more than one hour, up to and including 1, 3, 5, or more days).

In order to protect the adhesive characteristics of the anchor regions, the securement devices of the invention are manufactured to include a removable layer attached to those surfaces to which an adhesive layer has been applied. Just prior to use the removable layer(s) can be separated from (e.g., by peeling) the rest of the device, after which the removable layer(s) can be disposed of.

In some preferred embodiments, the articles are substantially planar when packaged, allowing for easy, dense packaging as single, individually packaged, preferably sterile, articles.

The securement devices of the invention include an adaptive retainer that can readily conform, or adapt, to the exterior shape of a medical article to be retained. The adaptive retainer is flexible in nature, due both in part to its structure and to the material used to form it. Suitably flexible, non-segmented materials include various natural and synthetic rubbers and soft plastics. For embodiments that employ segmented adaptive retainer, for example, when the segments are connected by flex elements such as living hinges, suitable materials include, for example, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics, and the like. However, any material can be utilized.

The securement devices of the invention are preferably integrally formed to comprise a unitary retainer. This can be accomplished in any of a variety of ways well known to those skilled in the art. For instance, the entire device can be injection molded in order to reduce fabrication costs. The devices, however, can comprise non-unitary construction, for example, by joining independently manufactured adaptive retainers and anchor regions or anchor pads.

To facilitate a complete understanding of the invention, the remainder of the detailed description describes adaptive medical article securement devices by reference to the drawings, wherein like elements among the embodiments are referenced with like numerals throughout the following description.

Figure 1B:
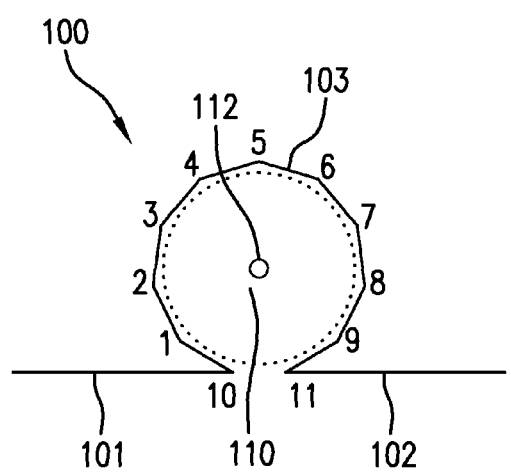
Figure 1C:
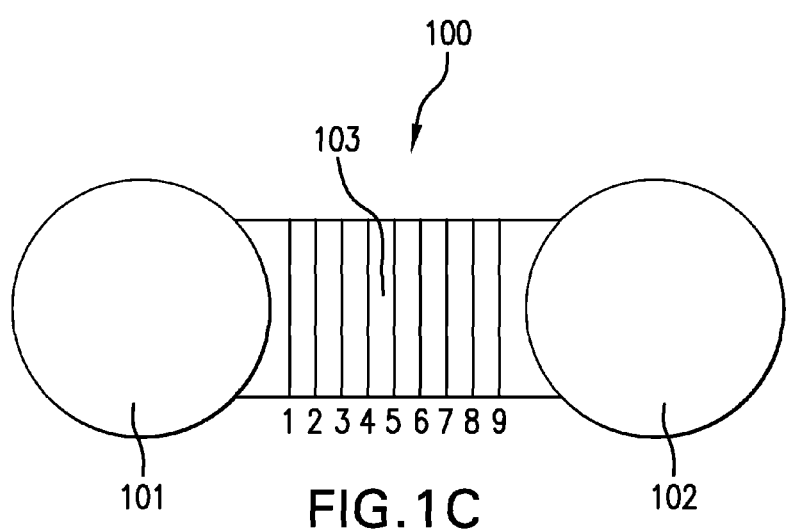

FIG. 1 shows three views of an adaptive medical article securement device (100). Panel A shows a side view of the securement device (100). The device has two anchor regions (101, 102) spaced apart by a flexible, substantially planar substrate (103) configured to deform to form a central channel (110) about a channel axis (112) upon application of a deforming force (not shown). In this embodiment, the substrate's flexibility is provided by several flex or hinge elements (1-11) that segment the substrate. Hinge elements 1-9 provide the capacity for the substrate to be deformed or folded into ten segments to retain a medical article by applying a deforming force to form a central channel (110). Hinge elements 10 and 11 demarcate the boundaries between the flexible substrate and the anchor regions (101, 102). The lower, or bottom, surface of each anchor region (101, 102) is coated with an adhesive (104) suited to attach the securement device to a patient's skin. Panel B shows the securement device after application of a deforming force, which results in the flexible substrate being folded to form an open central channel (110) comprised of 10 segments about a channel axis (112). Panel C shows a plan view of the securement device (100) of Panel A.

Figure 2A:
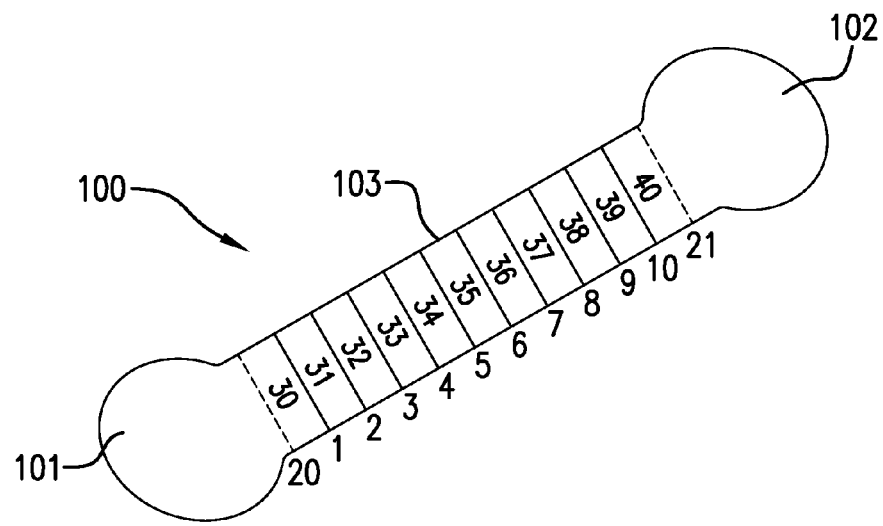
FIG. 2 has two panels, A and B. Panel A is a top view of a representative adaptive medical article securement device according to the invention prior to being adapted to receive a medical article, and Panel B is a perspective view of the securement device shown in Panel A after being adapted to receive a medical article.
Figure 2B:
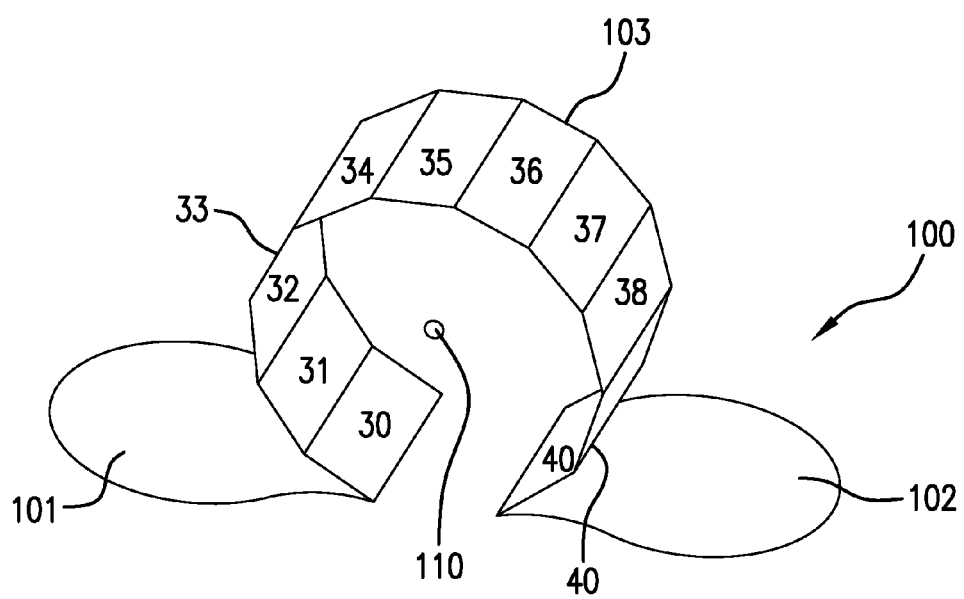

FIG. 2 shows two views, A and B, of an adaptive medical article securement device (100) that has a flexible, segmented substrate (103). Panel A shows the securement device in a substantially planar configuration. Panel B shows the device after it has been folded to form a central channel (110) to receive a medical article (not shown). In this embodiment, hinge elements 1-10, 20, and 21 provide the capacity for the substrate to be deformed or folded into eleven segments to retain a medical article by applying a deforming force to form the central channel.

Figure 3A:
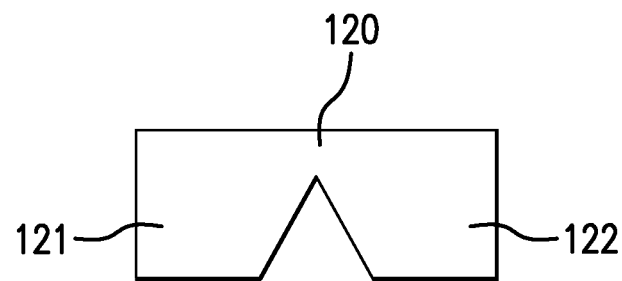
FIG. 3 has three panels, A, B, and C, showing three different "living hinge" cross-sections of representative adaptive medical article securement devices according to the invention.
Figure 3B:
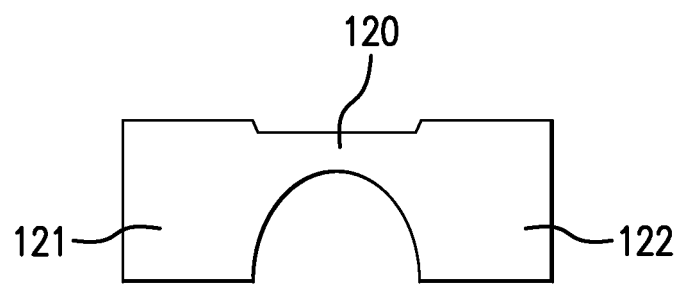
Figure 3C:
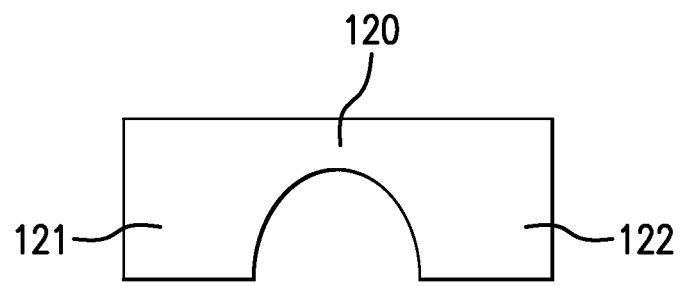

FIG. 3 shows three representative cross-sections, A, B, and C, of a "living hinge", a preferred flex or hinge element useful in practicing the invention. A living hinge is a thin, flexible hinge (a flexure bearing, 120) made from plastic that joins two rigid plastic parts (121, 122) together, allowing the plastic to bend in relation to each other along the line of the hinge (not shown). Living hinges are typically made in an injection molding process that creates all of the parts at one time as a single part. Polypropylene and polyethylene are particularly preferred plastics for fabricating parts with living hinges, such as adaptive retainers according to the invention. The thinned section (120) of the part allows for movement of the adjacent rigid plastic parts (121, 122) about the hinge line.

Figure 4A:
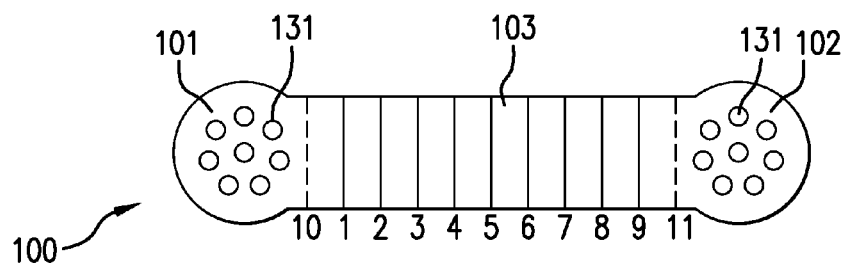
FIGS. 4 and 5 each have two panels, A and B. Each panel shows a top view of a different representative adaptive medical article securement device according to the invention.
Figure 4B:
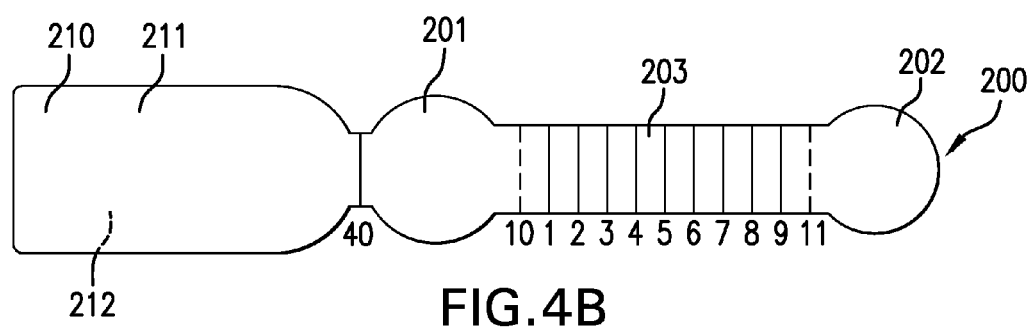

FIG. 4 shows two panels, A and B. The securement device shown in panel A is analogous to that shown in FIG. 1, panel C. In this embodiment, however, the anchor regions (101, 102) comprise a plurality of perforations (131) that extend through the adaptive retainer's substrate. Panel B shows an alternative embodiment of a securement device (200) that includes a adaptive retainer that has first and second anchors (201, 202) and a flexible substrate (203) with a plurality of hinge elements (1-11), nine of which are on the upper surface of the flexible substrate (203) and two of which (10, 11) are on the lower surface of the flexible substrate (203). Attached to the adaptive retainer via hinge region (40) is an anchor pad (210). When adaptive retainer and anchor pad (210) are folded about their joining hinge (40), preferably after adapting the adaptive retainer to mate with a medical article (e.g., a catheter hub) the upper surfaces of the first and second anchors (201, 202) of the adaptive retainer can be attached, preferably using an adhesive coated onto the upper surface of each of the first and second anchors (201, 202), to the upper surface (211) of the anchor pad (210). The anchor pad can then be used to attach the securement device to a patient's skin, preferably using a biocompatible adhesive coated on the lower surface (212) of the anchor pad (210).

Figure 5A:
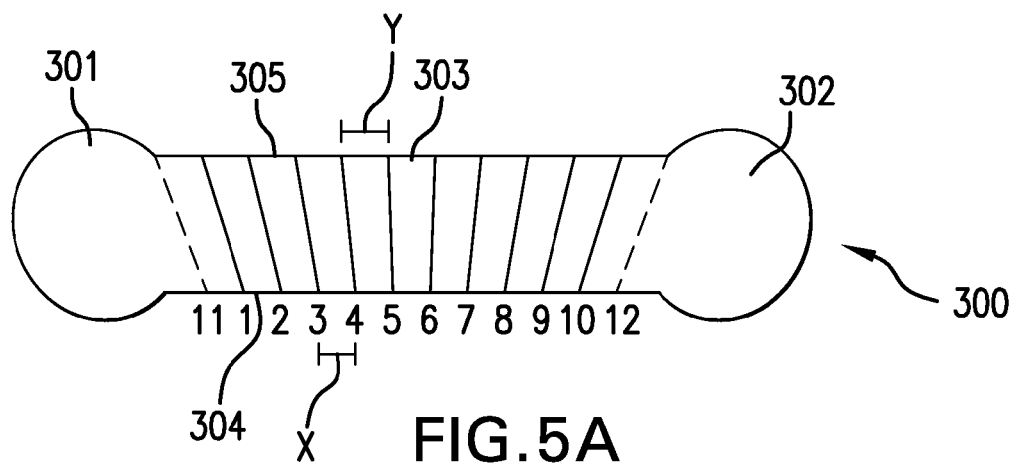
Figure 5B:
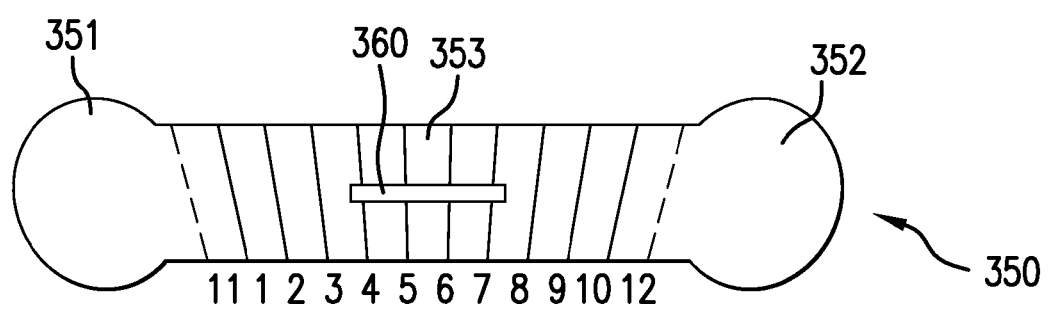

FIG. 5 shows two panels, A and B. Panel A shows an alternative embodiment of a securement device (300) that includes a adaptive retainer that has first and second anchors (301, 302) and a flexible substrate (303) with a plurality of hinge elements (1-12), ten of which (1-10) are on the upper surface of the flexible substrate (303) and two of which (11, 12) are on the lower surface of the flexible substrate (303). In this embodiment, the hinge elements are not substantially parallel to one another; instead, their separation (X) at the leading edge (304) of the flexible substrate (303) is less than their separation at the trailing edge (305) of the flexible substrate (303). As a result, when the flexible substrate is deformed so as to become adapted to receive or engage a medical article, a tapered central channel is formed such that the distal opening of the central channel in such an embodiment is larger than the proximal opening. As those in the art will appreciate, such configurations are well suited for engaging medical fittings that have tapered exterior surfaces.

Panel B of FIG. 5 shows an alternative embodiment of a securement device (350) that is similar to the embodiment depicted in Panel A of the figure, the difference being that in the embodiment shown in panel B, the adaptive retainer includes a slot-shaped engaging element (360) configured to engage a retention element (not shown) disposed on the surface of a medical article (not shown) so as to reduce or inhibit movement, optionally longitudinal and/or pitch and/or roll and/or yaw movement, of a medical article retainingly engaged by the adaptive retainer.

All of the devices, articles, systems, and methods described and claimed herein can be made and executed without undue experimentation in light of the specification and drawings. While the invention has been described in terms of preferred embodiments, it will be apparent to those of ordinary skill in the art that variations may be applied to the devices, articles, systems, and methods without departing from the spirit and scope of the invention. All such variations and equivalents apparent to those skilled in the art, whether now existing or later developed, are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An adaptive medical article securement device that comprises an adaptive retainer, wherein the adaptive retainer comprises a first anchor region spaced from a second anchor region by a flexible, segmented, substantially flat substrate bounded by first and second channel boundary hinge elements disposed on a lower surface of the segmented, substantially flat substrate, wherein the flexible, segmented, substantially flat substrate comprises a first plurality (n) of spaced channel hinge elements disposed on an upper surface thereof that define a second plurality (n-1) of discrete channel forming segments each bounded by two opposed spaced channel hinge elements, a leading edge, and a trailing edge opposite the leading edge, wherein the flexible, segmented, substantially flat substrate deforms to form a central channel about a channel axis upon application of a deforming force, the central channel (i) comprises a distal opening and a proximal opening and (ii) engages at least a portion of a medical article inserted into the central channel so as to retain the medical article, wherein a lower surface of each of the first and second anchor regions comprises an adhesive that attaches to an epidermal layer of a patient, wherein the adhesive is covered by a removable layer.

2. An adaptive medical article securement device according to claim 1 that further comprises at least one engaging element configured to engage a retention element disposed on the surface of the medical article so as to reduce or inhibit movement, longitudinal and/or pitch and/or roll and/or yaw movement of the medical article.

3. An adaptive medical article securement device according to claim 1 wherein the portion of the medical article engaged by the central channel is a catheter hub or connector fitting, optionally a luer access device.

4. An adaptive medical article securement device according to claim 1 wherein the central channel has an arc length of greater than 180 degrees.

5. An adaptive medical article securement device according to claim 1 wherein the central channel, once formed, has a tapered shape, wherein the tapered shape of the central channel, once formed, is configured to complement a cooperative tapered shape of the portion of the medical article to be disposed in the central channel.

6. A medical article securement system, comprising:
    a. an adaptive medical article securement device according to claim 1; and
    b. a medical article retained in the central channel of the adaptive medical article securement device.

7. A method of uniting a medical article with an adaptive medical article securement device, comprising deforming an adaptive medical article securement device according to claim 1 about at least a portion of a medical article so that the central channel of the adaptive medical article securement device retainingly engages the portion of a medical article, thereby uniting the medical article with the adaptive medical article securement device.

8. An adaptive medical article securement device that comprises an adaptive retainer connected to at least one anchor pad, wherein: (i) the adaptive retainer comprises a first anchor region spaced from a second anchor region by a flexible, segmented, substantially flat substrate bounded by first and second channel boundary hinge elements disposed on a lower surface of the segmented, substantially flat substrate, wherein the flexible, segmented, substantially flat substrate comprises a first plurality (n) of spaced channel hinge elements disposed on an upper surface thereof that define a second plurality (n-1) of discrete channel forming segments each bounded by two opposed spaced channel hinge elements, a leading edge, and a trailing edge opposite the leading edge, wherein the flexible, segmented, substantially flat substrate deforms to form a central channel about a channel axis upon application of a deforming force, the central channel (A) comprising a distal opening and a proximal opening and (B) that engages at least a portion of a medical article when inserted into the central channel so as to retain the medical article; and (ii) the at least one anchor pad comprises (A) a lower adhesive surface to attach the anchor pad(s) to an epidermal layer of a patient and (B) an upper surface at least a portion of which is adhered to the first or second anchor region.

9. An adaptive medical article securement device according to claim 8 that further comprises at least one engaging element configured to engage a retention element disposed on the surface of the medical article so as to reduce or inhibit movement, optionally longitudinal and/or pitch and/or roll and/or yaw movement of the medical article.

10. An adaptive medical article securement device according to claim 8 wherein the portion of the medical article engaged by the central channel is a catheter hub or connector fitting, optionally a luer access device.

11. An adaptive medical article securement device according to claim 8 wherein the central channel has an arc length of greater than 180 degrees.

12. An adaptive medical article securement device according to claim 8 wherein the central channel, once formed, has a tapered shape, wherein the tapered shape of the central channel, once formed, is configured to complement a cooperative tapered shape of the portion of the medical article to be disposed in the central channel.

13. A medical article securement system, comprising:
    a. an adaptive medical article securement device according to claim 8; and
    b. a medical article retained in the central channel of the adaptive medical article securement device.

14. A method of uniting a medical article with an adaptive medical article securement device, comprising deforming an adaptive medical article securement device according to claim 8 about at least a portion of a medical article so that the central channel of the adaptive medical article securement device retainingly engages the portion of a medical article, thereby uniting the medical article with the adaptive medical article securement device.

15. A method of securing a medical article to a patient, comprising uniting a medical article with an adaptive medical article securement device according to claim 8 and adhering the anchor pad(s) to a patient's skin.

* * * * *